United States Patent
Kang

(10) Patent No.: US 11,554,050 B2
(45) Date of Patent: Jan. 17, 2023

(54) CONTACTLESS EARPLUG DISPENSER

(71) Applicant: MOLDEX-METRIC, INC., Culver City, CA (US)

(72) Inventor: Sukwon Kang, Torrance, CA (US)

(73) Assignee: Moldex-Metric, Inc., Culver City, CA (US)

(*) Notice: Subject to any disclaimer, the term of this patent is extended or adjusted under 35 U.S.C. 154(b) by 211 days.

(21) Appl. No.: 17/145,139

(22) Filed: Jan. 8, 2021

(65) Prior Publication Data

US 2022/0219901 A1 Jul. 14, 2022

(51) Int. Cl.
| | | |
|---|---|---|
| *B65G 1/08* | (2006.01) |
| *A61F 11/08* | (2006.01) |
| *G07F 11/44* | (2006.01) |
| *H02K 11/28* | (2016.01) |
| *H02K 11/00* | (2016.01) |

(52) U.S. Cl.
CPC .......... *A61F 11/08* (2013.01); *B65G 1/08* (2013.01); *G07F 11/44* (2013.01); *H02K 11/0094* (2013.01); *H02K 11/28* (2016.01); *H02K 2211/03* (2013.01)

(58) Field of Classification Search
CPC .......... G07F 11/54; G07F 11/56; G07F 11/44; A65F 11/08; B65D 83/0083
USPC .................................................... 221/265, 7
See application file for complete search history.

(56) References Cited

U.S. PATENT DOCUMENTS

| | | | | | |
|---|---|---|---|---|---|
| 2,176,232 | A | * | 10/1939 | Warren ..................... | A47F 1/10 221/265 |
| 2,211,452 | A | * | 8/1940 | Bowman ................. | A47F 1/035 222/452 |
| 2,630,245 | A | * | 3/1953 | Maier ................ | B65D 83/0409 221/265 |
| 2,750,072 | A | * | 6/1956 | Edith ....................... | G01F 11/24 222/42 |
| 3,128,011 | A | * | 4/1964 | Bleiman ................. | G07F 11/44 221/68 |
| 3,330,442 | A | * | 7/1967 | O'connor ............... | A47G 19/34 221/265 |

(Continued)

FOREIGN PATENT DOCUMENTS

| | | | | |
|---|---|---|---|---|
| CA | 2882770 A1 | * | 3/2014 | ............ B65B 37/16 |
| DE | 69838884 T2 | * | 12/2008 | ............ B65B 5/103 |

(Continued)

OTHER PUBLICATIONS

Printed webpage from https://www.directindustry.com/—product, Dec. 4, 2020, pp. 1-2.

(Continued)

*Primary Examiner* — Rakesh Kumar
(74) *Attorney, Agent, or Firm* — Schwegman Lundberg & Woessner, P.A.

(57) ABSTRACT

An earplug dispenser for contactless operation by a user having a container portion for receiving a plurality of earplugs. A dispensing portion is coupled to the container portion. The dispensing portion has a motor and a rotor coupled to the motor. The rotor has a plurality of rotor openings to receive individual earplugs in each rotor opening. The dispensing portion also has a dispensing opening. The motor rotates the rotor to dispense earplugs through the dispensing opening.

20 Claims, 6 Drawing Sheets

(56) References Cited

U.S. PATENT DOCUMENTS

| | | | | |
|---|---|---|---|---|
| 3,785,525 A * | 1/1974 | Handeland | ......... | B65G 47/1471 221/265 |
| 3,822,004 A * | 7/1974 | Bolen, Jr. | ............... | G07F 11/44 221/265 |
| 3,885,703 A * | 5/1975 | Neavin | ............. | B65D 83/0409 221/202 |
| 4,109,825 A * | 8/1978 | Weitzman | ............... | G07F 11/54 221/14 |
| 4,530,447 A * | 7/1985 | Greenspan | ............ | B65D 83/04 222/543 |
| 4,662,538 A * | 5/1987 | Goudy, Jr. | ............. | C02F 1/687 221/265 |
| 5,097,985 A * | 3/1992 | Jones | .................. | A63B 47/002 221/277 |
| 5,259,532 A * | 11/1993 | Schwarzli | ............... | G07F 11/44 221/265 |
| 5,280,845 A * | 1/1994 | Leight | ................... | G07F 11/44 221/265 |
| 5,322,185 A * | 6/1994 | Leight | ................... | A61F 11/08 221/265 |
| 5,443,179 A | 8/1995 | Palmer et al. | | |
| 5,702,029 A * | 12/1997 | Yang | ........................ | G07F 13/10 221/221 |
| 5,785,206 A * | 7/1998 | Chan | ........................ | G07F 11/14 221/269 |
| 5,791,515 A * | 8/1998 | Khan | ................. | B65D 83/0409 221/265 |
| 5,794,816 A * | 8/1998 | Pliler | ...................... | G07F 11/44 221/265 |
| D413,465 S | 9/1999 | Smith et al. | | |
| 5,954,229 A * | 9/1999 | Scholey | .................. | A61F 11/08 221/265 |
| 6,241,120 B1 * | 6/2001 | Scholey | .................. | A61F 11/08 221/265 |
| 6,786,356 B2 * | 9/2004 | Geiger | .................... | A47J 31/60 99/290 |
| 7,404,500 B2 * | 7/2008 | Marteau | ............. | B65D 83/0409 221/229 |
| 7,896,198 B2 * | 3/2011 | Mehus | .................. | B01F 35/881 422/255 |
| 8,746,225 B2 * | 6/2014 | Christopher | ............ | F41B 11/53 124/51.1 |
| 9,010,585 B1 * | 4/2015 | Schultz | ................. | B65G 11/186 248/229.11 |
| 9,238,545 B2 * | 1/2016 | Bae | ......................... | G07F 11/44 |
| 10,292,906 B1 | 5/2019 | Gershoni et al. | | |
| 2002/0043538 A1 * | 4/2002 | Millar | ..................... | G07F 11/44 221/265 |
| 2002/0096535 A1 * | 7/2002 | Zhang | ..................... | B65B 35/26 221/265 |
| 2004/0099295 A1 * | 5/2004 | You | ........................ | F16B 7/1427 135/16 |
| 2007/0145066 A1 * | 6/2007 | Knoth | .................. | G07F 17/0092 221/265 |
| 2011/0042404 A1 * | 2/2011 | Koike | ..................... | G07F 11/44 221/258 |
| 2015/0027286 A1 * | 1/2015 | Yuyama | .................... | A61J 7/02 83/105 |
| 2015/0179018 A1 * | 6/2015 | Rudek | .................. | A61F 15/001 221/186 |
| 2016/0001955 A1 * | 1/2016 | Wang | .................. | B65D 83/0409 221/268 |
| 2018/0161247 A1 * | 6/2018 | Koike | .................. | A61J 7/0076 |

FOREIGN PATENT DOCUMENTS

| | | | | |
|---|---|---|---|---|
| EP | 1035035 A1 * | 9/2000 | ......... | B65D 83/0409 |
| EP | 1074236 A2 * | 2/2001 | ........... | A61F 15/001 |
| EP | 2754431 | 7/2014 | | |
| EP | 3002737 | 4/2016 | | |
| EP | 4027312 A1 * | 7/2022 | ............... | B65G 1/08 |
| WO | 8700743 | 2/1987 | | |
| WO | 2016003649 | 1/2016 | | |

OTHER PUBLICATIONS

"European Application Serial No. 21214598.1, Extended European Search Report dated May 30, 2022", 9 pgs.

* cited by examiner

CONTACTLESS EARPLUG DISPENSER

BACKGROUND

The present invention relates to earplug dispensers and specifically to an earplug dispenser to allow a user to easily dispense earplugs when desired without having to touch the dispenser.

In the prior art, earplug dispensers have generally required a user to mechanically manipulate the dispenser to dispense the earplugs. This may allow for dirt and germs to be transferred between users of the dispenser. Accordingly it would be desirable to provide for the dispensing of earplugs without users having to contact the dispenser. Additionally, it would be desirable to provide for the dispensing of earplugs in a consistent, reliable and predictable way.

SUMMARY

The present invention includes a structure for contactless dispensing of earplugs that remedies the shortcomings of the prior art. According to an implementation, an earplug dispenser for contactless operation by a user has a container portion with a plurality of earplugs; and a dispensing portion coupled to the container portion. The dispensing portion has a motor; a rotor coupled to the motor, the rotor having a plurality of rotor openings to receive individual earplugs in each rotor opening; and a dispensing opening. The motor rotates the rotor to dispense earplugs through the dispensing opening. In an implementation, the dispenser also has an individual dispensing structure located adjacent each rotor opening to dispense individual earplugs to the dispensing opening in a consistent, reliable and predictable way.

In an implementation, the dispenser has a plurality of gates positioned proximal to the plurality of rotor openings, each gate being separately movable between a first position and a second position as the rotor is rotated to dispense an earplug. The contactless earplug dispenser may have a cam with a raised portion proximal to the dispensing opening. Each of the plurality of gates has a follower that travels along the cam as the rotor rotates. The raised portion of the cam pushes up on the follower to pivot the gate downward to dispense an earplug from the rotor opening through the dispenser opening.

In an implementation, the dispenser also has a mount couplable to a surface; wherein the mount and the dispensing portion have reciprocal structures to allow the dispensing portion to be slid into the mount to be received and supported so that the dispensing portion extends downwardly. The dispenser may also have at least one battery in electrical communication with the motor. The container portion may be made of transparent material so that the quantity of earplugs is visible.

The dispenser may also have a circuit board in electrical communication with the motor; and a hand sensor positioned proximal to the dispensing opening to detect the presence of a user's hand below the dispensing opening, the hand sensor being in electrical communication with the circuit board. The circuit board may be configured to provide power to the motor when a user's hand is detected by the hand sensor. The dispenser may also have a counting sensor positioned proximal to the dispenser opening and in electrical communication with the circuit board. The circuit board may be configured to cease providing power to the motor upon detection of a predetermined number of earplugs passing by the counting sensor. In an implementation, the motor is reversible and the circuit board is configured to reverse the direction of the motor when the counting sensor fails to detect any earplugs for a predetermined time, such as a few seconds. In an implementation, the motor is reversible and the circuit board is configured to reverse the direction of the motor when the counting sensor detects an earplug.

In an implementation, the rotor has an upper rotor coupled to a lower rotor. The upper rotor may have a central raised portion forming a hump to guide the earplugs to the rotor openings; and a plurality of upstanding ridges to stir the earplugs from the container portion.

In an additional implementation of the invention, an earplug dispenser for contactless operation by a user has a container portion for receiving a plurality of earplugs; and a dispensing portion coupled to the container portion such that the dispensing portion is positioned below the container portion and gravity causes the earplugs in the container portion to fall into the dispensing portion. The dispensing portion has a motor; a rotor coupled to the motor, the rotor having a plurality of rotor openings to receive individual earplugs in each rotor opening. A plurality of gates are positioned proximal to the plurality of rotor openings. Each gate is separately movable between a first position and a second position as the rotor is rotated to dispense an earplug. The dispensing portion also has a dispensing opening.

At least one battery is in electrical communication with the motor. A circuit board in electrical communication with the motor and with the battery; and a hand sensor is positioned proximal to the dispensing opening to detect the presence of a user's hand below the dispensing opening. The hand sensor is in electrical communication with the circuit board. The circuit board is configured to provide power to the motor when a user's hand is detected by the hand sensor. The motor rotates the rotor and the plurality of gates to dispense earplugs through the dispensing opening. The contactless earplug dispenser may also have a counting sensor positioned proximal to the dispenser opening and in electrical communication with the circuit board; and the circuit board may be configured to cease providing power to the motor upon detection of a predetermined number of earplugs passing by the counting sensor.

These and other features are described below.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

Figure 1:
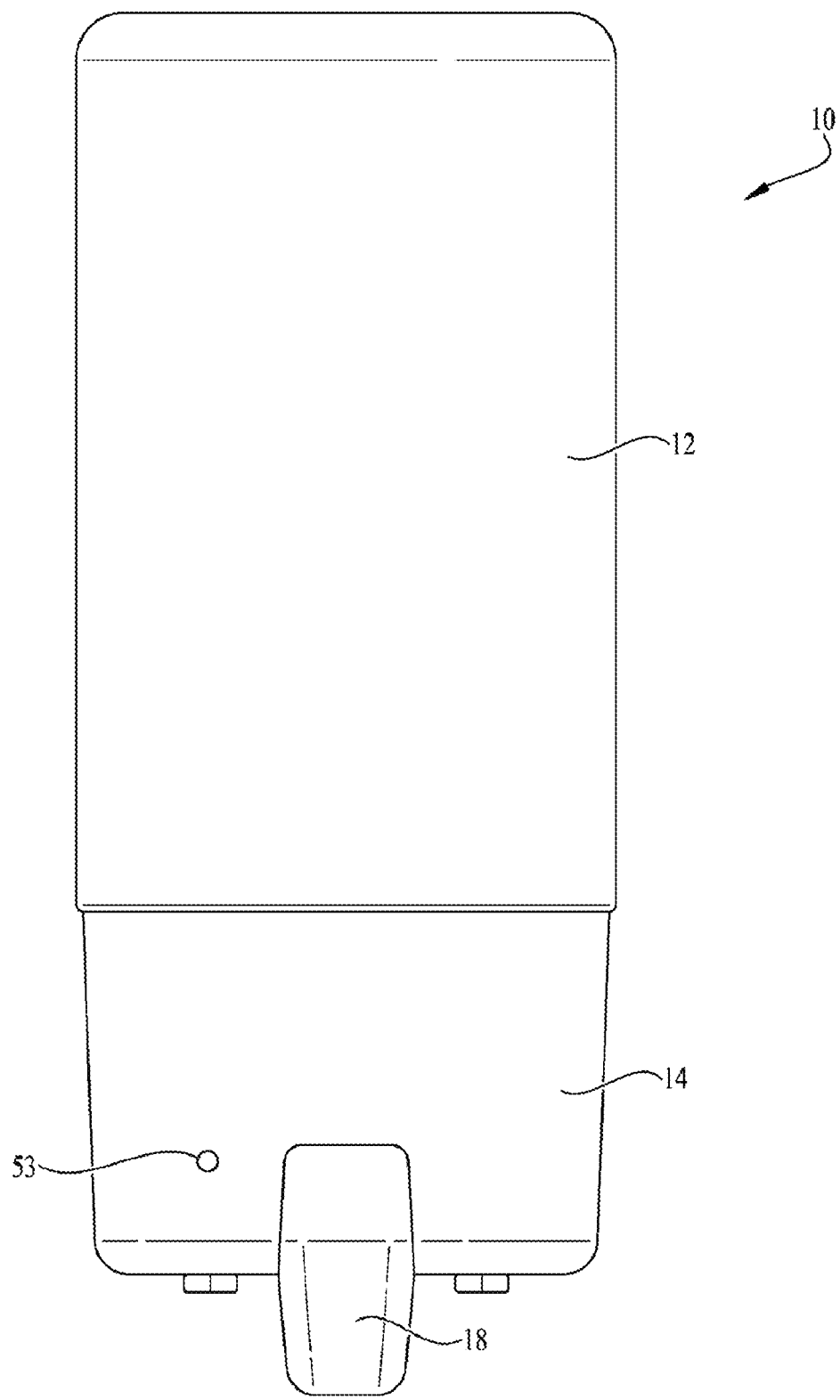
FIG. 1 is a front elevation view of a contactless earplug dispenser according to an implementation of the present invention.

As shown in FIG. 1, an earplug dispenser 10 according to an implementation of the present invention has a container portion 12 and a dispensing portion 14. The container portion 12 may be a transparent plastic bottle to allow a user to see whether earplugs 16 remain in the dispenser 10. The container portion 12 may interlock with the dispensing portion 14, such as, for example, by threads or a snap fit. The earplugs 16 are dispensed from the container portion 12 through a dispensing opening 18 in the dispensing portion 14 onto the hand of a user.

Figure 2:
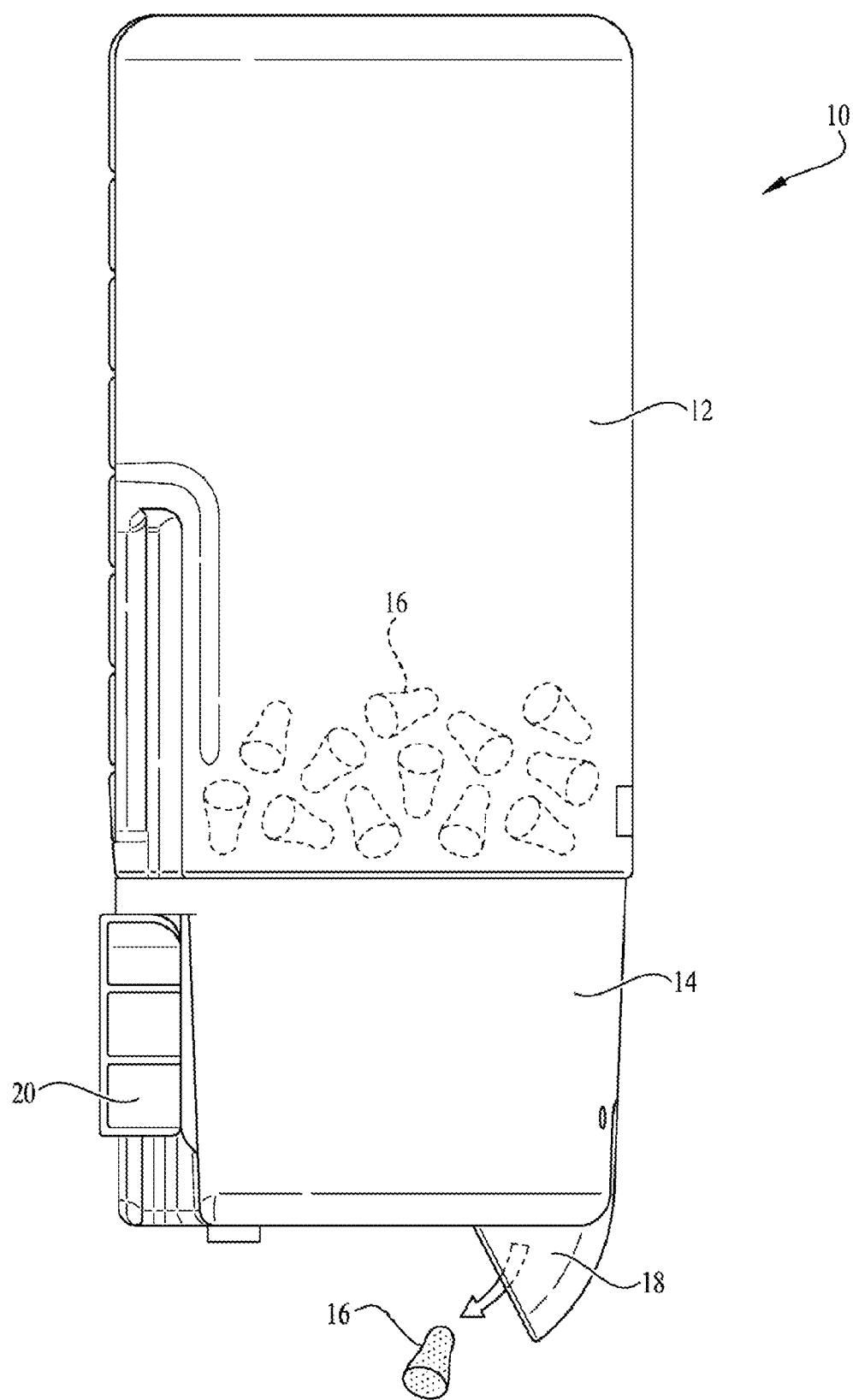
FIG. 2 is a side elevation view of the contactless earplug dispenser of FIG. 1.
Figure 3:
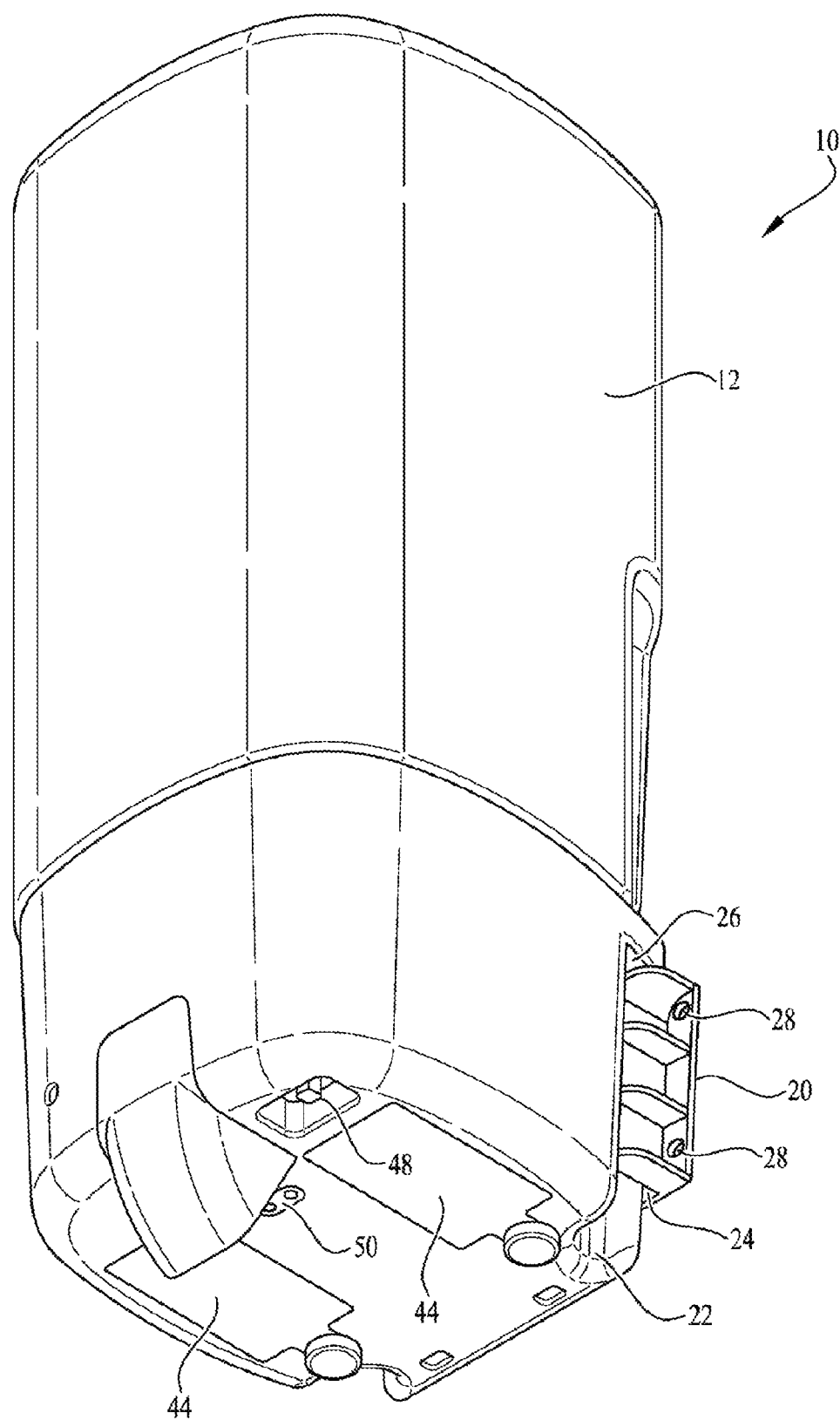
FIG. 3 is a perspective view of the contactless earplug dispenser of FIG. 1.

As shown in FIGS. 2 to 5, the dispensing portion 14 is removably coupled to a mount 20 using integral flanges 22 formed at the back of the dispensing portion. The flanges 22 slide into a recess 24 formed in the mount 20. As seen in FIG. 3, the dispensing portion 14 is insertable into the mount 20 until a stop surface 26 formed on the dispensing portion 14 engages an upper surface of the mount. In an implementation, the mount may be coupled to a wall using a plurality of fasteners 28. In an additional implementation the mount 20 may be configured to couple to a horizontal surface, such as a tabletop.

The container portion 12 fits into the dispensing portion 14 to seal the contents of the container portion 12 except for the dispensing opening 18 which controllably allows the earplugs 16 to fall into the hand of the user. The dispensing portion 14 may be permanently attached to the container portion 12 so that the entire container portion and all of the earplugs contained therein form one disposable unit. Alternatively, the container portion 12 may be initially sealed with a temporary cap. When the earplugs 16 are to be dispensed, the temporary cap may be removed and the container portion 12 placed into the dispensing portion 14. Once the container portion 12 is placed into the dispensing portion 14, the unit may then be turned upside down and inserted into the mount 20 as shown in FIGS. 2 and 3.

The dispensing portion 14 is constructed to receive and hold in position a controllably motorized impeller system 30. The impeller system 30 moves the earplugs 16 from a storage position within the container portion 12 to the dispensing opening 18 in the dispensing portion 14 and ultimately to the hand of a user. The impeller system 30 has an upper rotor 32 coupled to a lower rotor 34. The lower rotor 34 has a plurality of openings 36 that are covered with moveable gates 38. In an implementation, the lower rotor 34 has five openings 36 positioned about 72 degrees apart. The lower rotor 34 is coupled to a gear box 40 driven by a motor 42.

In an implementation, the motor 42 is powered by one or more batteries stored in the dispensing portion 14. In an implementation, as shown in FIG. 3, a lower surface of the dispensing portion 14 has two removeable battery doors 44. Four AA batteries may be placed in battery compartments in the dispensing portion 14. In an additional implantation, four AAA batteries may be used to power the motor 42. In an additional implementation, the dispenser 10 may be connected to an external supply to power the motor 42.

The motor 42 is in electrical communication with and controlled by a printed circuit board 46 with a microcontroller. For example, the microcontroller may be a Singapore Changi Technology (SCMCU) SC8F2792 microcontroller.

The printed circuit board 46 is in electrical communication with a power switch 48 and a hand sensor 50 positioned on a lower surface of the dispensing portion 14. In an implementation, the hand sensor 50 has an infrared (IR) transmitter and receiver from Y. Lin Electronics in Guangdong, China. The printed circuit board 46 is also in electrical communication with a count sensor 52 positioned proximal to the opening 18 in the dispensing portion 14 and configured to sense each of the earplugs 16 passing through the opening. In an implementation, the count sensor 52 has an infrared (IR) transmitter and receiver from Y. Lin Electronics in Guangdong, China. In an implementation, the printed circuit board 46 is also in electrical communication with a status light 53.

Figure 4:
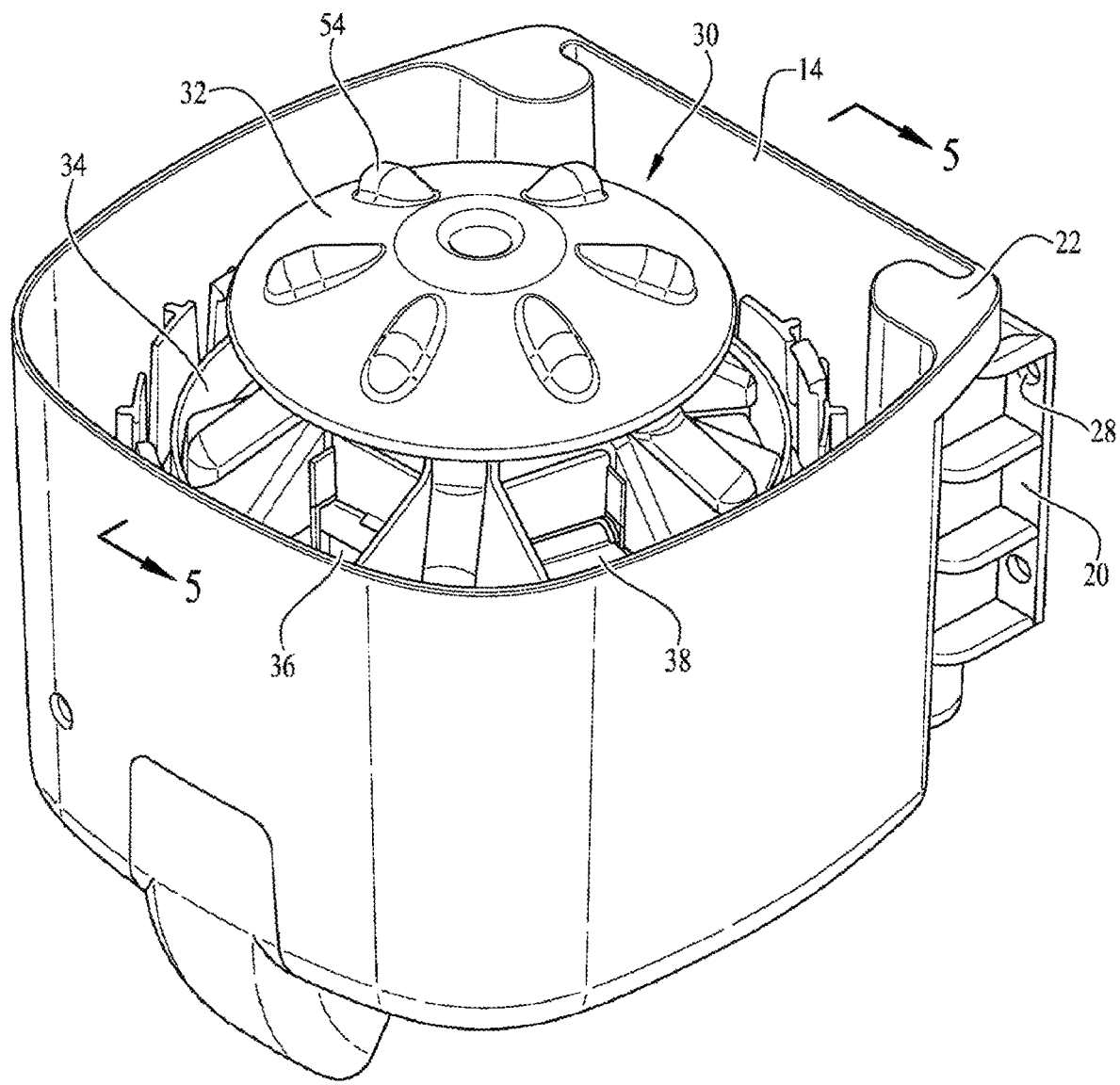
FIG. 4 is a perspective view of the contactless earplug dispenser of FIG. 1 with the container portion removed.
Figure 5:
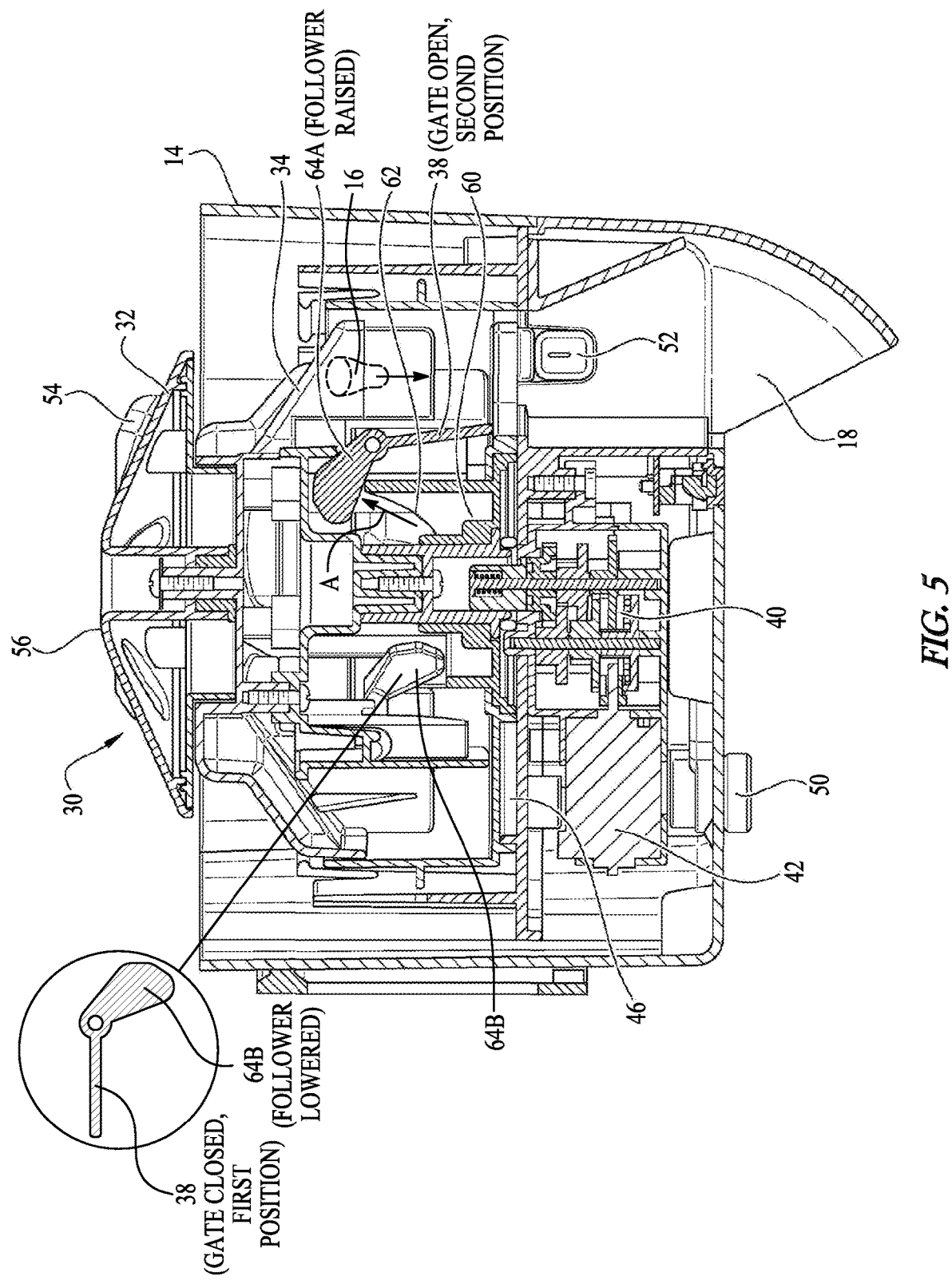
FIG. 5 is a cross sectional view taken along lines 5-5 of FIG. 4.

FIG. 4 shows a top perspective view of the dispensing portion 14 and the impeller system 30. FIG. 5 is a cutaway view showing the structure of FIG. 4 along line 5-5. As can be seen in FIG. 4, the upper rotor 32 includes a plurality of upstanding ridges 54 spaced equally around a circumference of the upper rotor. The central portion of the upper rotor 32 is formed as a hump 56 to gently guide the earplugs down into the openings 36 in the lower rotor 34. The upper rotor 32 prevents earplugs 16 from jamming on the lower rotor by dispersing and limiting the flow of earplugs. The ridges 54 also tend to stir up the earplugs 16 to assist in moving the earplugs down the slope of the hump 56 between the ridges to openings 36. This is accomplished as the upper rotor 32 and lower rotor 34 are rotated by motor 42 and gear box 40.

The lower rotor 34 rotates around a cam 60. In an implementation, the cam 60 has a raised engagement surface 62 positioned proximal to the dispensing opening 18. Each moveable gate 38 has a follower 64 that moves along the cam 60. As the follower 64 travels along the raised engagement surface 62, the cam 60 pushes up on the follower and causes the moveable gate 38 to pivot downward to allow an earplug 16 to pass through the lower rotor opening 36 (see for example the falling earplug 16 in FIG. 5) and into the dispensing opening 18. FIG. 5 shows one moveable gate 38 pivoted, by movement of the follower 64A along and up the raised (upwardly curved) engagement surface 62 in the direction of arrow A, to a downward, open (or second) position proximal to the dispensing opening 18. The inset view of FIG. 5 shows another gate 38 in an upward, closed (or first) position in which the gate 38 blocks passage of an earplug 16. The follower 64B in the inset view is in a lowered position, unaffected by the raised engagement surface 62 positioned proximal to the dispensing opening 18.

The dispenser 10 is placed in the mount 20 by sliding the flanges 22 of the dispensing portion 14 into the recess 24 of the mount until the stop surface 26 engages an upper surface of the mount. Once mounted, the dispenser is powered on by moving the power switch 48 from an off position to an on position. In an implementation, once powered on, the status light 53 illuminates for at least a preselected time. In an implementation, if the battery is low, then the printed circuit board 46 may cause the status light 53 to change colors or blink.

Figure 6:
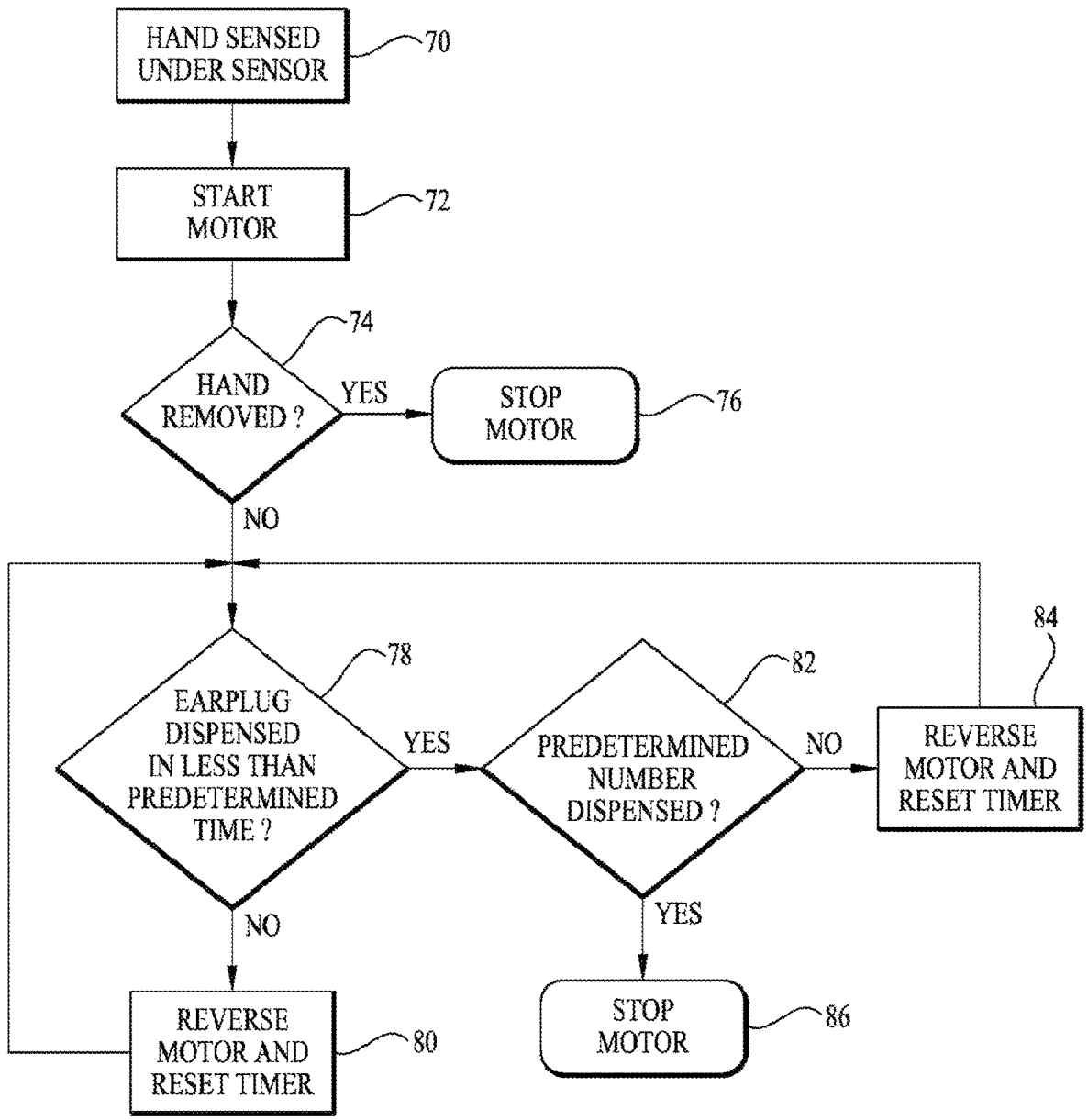
FIG. 6 is a flow chart illustrating operation of a contactless earplug dispenser according to an implementation of the present invention.

Operation of the dispenser 10 will now be described with reference to FIG. 6. Once powered on, the dispenser waits for detection of a user's hand by the hand sensor 50, Box 70. Once a user's hand is detected by the hand sensor 50, the motor is engaged to rotate the upper rotor 32 and the lower rotor 34, Box 72. Earplugs 16 move from the container portion 12 over the upper rotor 32, into openings 36 in the lower rotor 34, and ultimately through the dispensing opening, past the count sensor 52 and into the hand of a user. The hand sensor 50 continuously senses for the presence of a user's hand, Box 74. If the hand sensor 50 ceases to detect a user's hand prior to dispensing the predetermined number of earplugs, then the circuit board causes the motor to cease operation, Box 76.

Once engaged, the motor rotates in a first direction until an earplug 16 is dispensed or until a predetermined time has elapsed, Box 78. If no earplugs 16 are detected by the count sensor 52 after the preselected time then the printed circuit board 46 causes the motor 42 and gear box 40 to reverse directions and resets the timer, Box 80. Reversing directions assists in agitating the earplugs 16 to aid in dispensing. In an implementation, the predetermined time is between about 3 seconds and about 7 seconds, and in a preferred implementation, between about 4 and about 5 seconds.

If an earplug is detected by the count sensor 52 then the printed circuit board determines whether a predetermined number of earplugs 16 have been dispensed, Box 82. The predetermined number of earplugs 16 may be a single earplug, two earplugs, or more than two earplugs. If the predetermined number of earplugs 16 has not yet been dispensed, then the motor is reversed and the timer reset, Box 84. Once the predetermined number of earplugs 16 have been detected by the count sensor 52, then the printed circuit board causes the motor to cease operation, Box 86.

In an implementation, the predetermined number of earplugs 16 to be dispensed is two and the printed circuit board 46 causes the motor 42 and gear box 40 to reverse directions after one earplug has been detected by the count sensor 52. Reversing the motor reduces jamming and helps dispense earplugs in a consistent, reliable and predictable way.

In an additional implementation, the system may be constructed without moveable gates and the rotor may be structured such as disclosed in U.S. Pat. Nos. 5,954,229 and 6,241,120, the entire contents of which are hereby incorporated herein by reference. The earplugs 16 may move from a storage position within the container portion 12 into the openings 36 of the lower rotor 34. Once the opening 36 with the earplug 16 reaches the dispensing opening, the earplugs 16 may fall from the opening through the dispensing opening.

The present intention therefore is directed to a contactless earplug dispenser which is preferably wall-mounted but could also be table mounted and with the container portion for the earplugs being a transparent container. The entire dispenser may be disposable or may have a disposable portion and a reusable portion. The dispensing portion is inserted into the mount to allow for simple and easy dispensing of earplugs to a user by merely placing a hand under the dispensing portion and allowing earplugs to drop into the hand of the user.

The design of the earplug dispenser of the present invention is relatively inexpensive so that the dispenser may be completely disposable including the dispensing portion. Each time a disposable earplug dispenser is inserted into the mount, a fresh dispensing portion is provided Which would tend to eliminate any problems of wear or other failures that can occur over time as a structure is being used on a regular basis. The present invention provides for a simple structure and a structure which eliminates the problem of users getting dirt or germs on a dispenser through contact. Additionally, the structure of the earplug dispenser of the present invention dispenses earplugs in a consistent, reliable and predictable way.

There is disclosed in the above description and the drawings, a contactless earplug dispenser that fully and effectively overcomes the disadvantages associated with the prior art. However, it will be apparent that variations and modifications of the disclosed implementations may be made without departing from the principles of the invention. The presentation of the preferred implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An earplug dispenser for contactless operation by a user comprising:
   a container portion further comprising a plurality of earplugs;
   a dispensing portion coupled to the container portion, the dispensing portion further comprising:
   a motor;
   a rotor coupled to the motor, the rotor comprising a plurality of rotor openings to receive individual earplugs in each rotor opening;
   a dispensing opening, wherein the motor rotates the rotor to dispense earplugs through the dispensing opening;
   a plurality of gates positioned proximal to the plurality of rotor openings, each gate being separately movable between a first, closed position and a second, open position as the rotor is rotated to dispense an earplug;
   a cam having a raised portion proximal to the dispensing opening;
   wherein each of the plurality of gates has a follower that travels along the cam as the rotor rotates; and wherein the raised portion of the cam pushes up on the follower to pivot a respective gate to a respective second, open position to dispense an earplug through the dispenser opening.

2. The earplug dispenser of claim 1 further comprising a mount couplable to a surface; wherein the mount and the dispensing portion further comprise reciprocal structures to allow the dispensing portion to be slid into the mount to be received and supported so that the dispensing portion extends downwardly.

3. The earplug dispenser of claim 1 further comprising at least one battery in electrical communication with the motor.

4. The earplug dispenser of claim 1 further comprising:
   a circuit board in electrical communication with the motor; and
   a hand sensor positioned proximal to the dispensing opening to detect the presence of a user's hand below the dispensing opening, the hand sensor being in electrical communication with the circuit board;
   wherein the circuit board is configured to provide power to the motor when a hand is detected by the hand sensor.

5. The earplug dispenser of claim 1 further comprising a counting sensor positioned proximal to the dispenser opening and in electrical communication with the circuit board; wherein the circuit board is configured to cease providing power to the motor upon detection of a predetermined number of earplugs passing by the counting sensor.

6. The earplug dispenser of claim 5 wherein the motor is reversible and the circuit board is configured to reverse the direction of the motor when the counting sensor fails to detect any earplugs for a predetermined time.

7. The earplug dispenser of claim 5 wherein the motor is reversible and the circuit board is configured to reverse the direction of the motor when the counting sensor detects an earplug.

8. The earplug dispenser of claim 1 further comprising a counting sensor positioned proximal to the dispenser opening and in electrical communication with the circuit board;
   wherein the motor is reversible and the circuit board is configured to reverse the direction of the motor when the counting sensor fails to detect any earplugs for a predetermined time.

9. The earplug dispenser of claim 1 further comprising a counting sensor positioned proximal to the dispenser opening and in electrical communication with the circuit board;
   wherein the motor is reversible and the circuit board is configured to:
   reverse the motor when the counting sensor detects an earplug; and
   cease providing power to the motor upon detection of a predetermined number of earplugs passing by the counting sensor.

10. The earplug dispenser of claim 9 wherein the circuit board is further configured to reverse the direction of the motor when the counting sensor fails to detect any earplugs for a predetermined time.

11. The earplug dispenser of claim 1 wherein the container portion is made of transparent material so that the quantity of earplugs is visible.

12. The earplug dispenser of claim 1 wherein the rotor comprises an upper rotor coupled to a lower rotor; and wherein the upper rotor further comprises:
   a central raised portion forming a hump to guide the earplugs to the rotor openings; and
   a plurality of upstanding ridges to stir the earplugs from the container portion.

13. An earplug dispenser for contactless operation by a user comprising:
   a container portion for receiving a plurality of earplugs;
   a dispensing portion coupled to the container portion such that the dispensing portion is positioned below the container portion and gravity causes the earplugs in the container portion to fall into the dispensing portion, the dispensing portion further comprising:
   a motor;
   a rotor coupled to the motor, the rotor comprising a plurality of rotor openings to receive individual earplugs in each rotor opening;
   a plurality of gates positioned proximal to the plurality of rotor openings, each gate being separately movable between a first position and a second position as the rotor is rotated to dispense an earplug;
   a dispensing opening;
   at least one battery in electrical communication with the motor;
   a circuit board in electrical communication with the motor and with the battery; and
   a hand sensor positioned proximal to the dispensing opening to detect the presence of a user's hand below the dispensing opening, the hand sensor being in electrical communication with the circuit board;
   wherein the circuit board is configured to provide power to the motor when a user's hand is detected by the hand sensor; and
   wherein the motor rotates the rotor and the plurality of gates to dispense earplugs through the dispensing opening.

14. The earplug dispenser of claim 13 further comprising a counting sensor positioned proximal to the dispenser opening and in electrical communication with the circuit board;
   wherein the circuit board is configured to cease providing power to the motor upon detection of a predetermined number of earplugs passing by the counting sensor.

15. The earplug dispenser of claim 13 further comprising a counting sensor positioned proximal to the dispenser opening and in electrical communication with the circuit board;
   wherein the motor is reversible and the circuit board is configured to reverse the direction of the motor when the counting sensor fails to detect any earplugs for a predetermined time.

16. The earplug dispenser of claim 13 further comprising a counting sensor positioned proximal to the dispenser opening and in electrical communication with the circuit board;
   wherein the motor is reversible and the circuit board is configured to reverse the direction of the motor when the counting sensor detects an earplug.

17. The earplug dispenser of claim 13 further comprising a counting sensor positioned proximal to the dispenser opening and in electrical communication with the circuit board;
   wherein the motor is reversible and the circuit board is configured to:
   reverse the direction of the motor when the counting sensor fails to detect any earplugs for a predetermined time;
   reverse the motor when the counting sensor detects an earplug; and
   cease providing power to the motor upon detection of a predetermined number of earplugs passing by the counting sensor.

18. The earplug dispenser of claim 13 further comprising a mount couplable to a surface; wherein the mount and the dispensing portion further comprise reciprocal structures to allow the dispensing portion to be slid into the mount to be received and supported so that the dispensing portion extends downwardly.

19. The earplug dispenser of claim 13 wherein the rotor comprises an upper rotor coupled to a lower rotor; and wherein the upper rotor further comprises:
   a central raised portion forming a hump to guide the earplugs to the rotor openings; and
   a plurality of upstanding ridges to stir the earplugs from the container portion.

20. The earplug dispenser of claim 13 further comprising a cam having a raised portion proximal to the dispensing opening;
   wherein each of the plurality of gates has a follower that travels along the cam as the rotor rotates; and wherein the raised portion of the cam pushes up on the follower to pivot the gate downward to dispense an earplug from the rotor opening through the dispenser opening.

* * * * *

UNITED STATES PATENT AND TRADEMARK OFFICE
CERTIFICATE OF CORRECTION

| | |
|---|---|
| PATENT NO. | : 11,554,050 B2 |
| APPLICATION NO. | : 17/145139 |
| DATED | : January 17, 2023 |
| INVENTOR(S) | : Sukwon Kang |

It is certified that error appears in the above-identified patent and that said Letters Patent is hereby corrected as shown below:

In the Specification

In Column 5, Line 55, delete "Which" and insert --which-- therefor

Signed and Sealed this
Twenty-third Day of January, 2024

Katherine Kelly Vidal
*Director of the United States Patent and Trademark Office*